United States Patent [19]
Ozaki et al.

[11] Patent Number: 5,773,240
[45] Date of Patent: Jun. 30, 1998

[54] OPTICALLY ACTIVE α-SUBSTITUTED CARBOXYLIC ACID DERIVATIVES AND METHOD FOR PRODUCING THE SAME

[75] Inventors: Eiji Ozaki; Toshitaka Uragaki, both of Hiroshima; Keiichi Sakashita, Tokyo; Tetsuya Ikemoto, Hiroshima; Yoshimasa Kobayashi, Tokyo; Akihiro Sakimae, Hiroshima, all of Japan

[73] Assignee: Mitsubishi Rayon Co., Ltd., Tokyo, Japan

[21] Appl. No.: 750,761

[22] PCT Filed: Jun. 13, 1995

[86] PCT No.: PCT/JP95/01176

§ 371 Date: Dec. 12, 1996

§ 102(e) Date: Dec. 12, 1996

[87] PCT Pub. No.: WO95/34525

PCT Pub. Date: Dec. 21, 1995

[30] Foreign Application Priority Data

Jun. 13, 1994 [JP] Japan .................................. 6-130590
Jun. 16, 1994 [JP] Japan .................................. 6-134700
Mar. 24, 1995 [JP] Japan .................................. 7-66416

[51] Int. Cl.$^6$ .............................. C12P 1/00; C12P 7/44; C07C 69/34
[52] U.S. Cl. .......................... 435/41; 435/135; 435/142; 560/190; 560/201; 562/571
[58] Field of Search .................................. 562/400, 401, 562/480, 482, 571; 435/19, 29, 41, 135, 136, 142; 560/190, 201

[56] References Cited

U.S. PATENT DOCUMENTS

| | | | |
|---|---|---|---|
| 3,953,494 | 4/1976 | Meyers et al. ................................. | 560/1 |
| 4,294,775 | 10/1981 | McKinnie ................................. | 558/255 |
| 4,529,810 | 7/1985 | Stoutamire ................................. | 560/105 |
| 4,654,432 | 3/1987 | Fikentscher et al. .................. | 558/357 |
| 5,015,764 | 5/1991 | Manimaran et al. .................. | 562/401 |
| 5,248,608 | 9/1993 | Van Dooren et al. .................. | 435/280 |

FOREIGN PATENT DOCUMENTS

| | | |
|---|---|---|
| 0 513 806 | 11/1992 | European Pat. Off. . |
| 54-144252 | 9/1979 | Japan . |
| 59-21599 | 5/1984 | Japan . |
| 59-21600 | 5/1984 | Japan . |
| 60-16235 | 4/1985 | Japan . |
| 61-12676 | 4/1986 | Japan . |
| 64-67190 A | 3/1989 | Japan . |
| 2-195890 | 8/1990 | Japan . |
| 3-47092 A | 2/1991 | Japan . |

OTHER PUBLICATIONS

Aldrich, Aldrich Chemical Company (catalog), 1994, Nihonbashi Horidomecho, Chuo–ku, Tokyo 103.
Albisetti, C.J., et al., "Dimers of Methacrylic Compounds," J. Am. Chem. Soc., 78:472–475 (1956).
House, H.O., "Modern Synthetic Reactions," Georgia Institute of Technology, W.A. Benjamin, Inc. (2nd ed., 1972), pp. 1–11.
Barnett & Morris, 1946, *Biochem.* 40:450–453.
J.H. Brewster, 1951, *J. of American Chem. Soc.* 73:366–370.
K.H. Engel, 1991, *Tetrahedron: Asymmetry* 2:165–168.
Guibe–Jampel et al., 1987, *J. Chem. Soc. Chem. Commun.* pp. 1080–1081.
Masegawa et al., 1984, *Chem Abstracts* 100:432, abstr. 84263g.
Morimoto et al., 1993, *Chem. Pharm. Bull.* 41:1149–1156.
Murakami et al., 1991, *Fermentations* 115:642, abstr. 115:69949b.
G. Ställberg, 1957, *Arkiv For Kemi* 12:153–159.
Derwent WPI Acc No 90–278847/37.
Derwent WPI Acc No 81–36564D/21.
Derwent WPI Acc No 89–124808/17 (1989).
Derwent WPI ACC No 90–306781/41 (1990).

*Primary Examiner*—Ponnathapura Achutamurthy
*Attorney, Agent, or Firm*—Pennie & Edmonds LLP

[57] ABSTRACT

The present invention relates to an optically active α-substituted carboxylic acid derivative represented by the general formula (I):

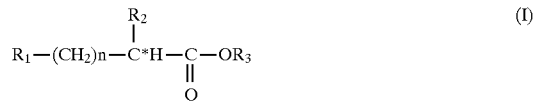

(wherein $R_1$ is a hydroxyl group,

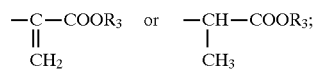

$R_2$ is a methyl group or a chlorine atom; $R_3$ is a hydrogen atom or an alkyl group with 1–6 carbon atoms; n is an integer of 1 or 2; and * represents an asymmetric carbon atom, provided that $R_2$ is a chlorine atom when $R_1$ is a hydroxyl group);

and a method for producing the optically active α-substituted carboxylic acid derivative represented by the general formula (I) and antipodes thereof using a culture, cells or a material obtainable from cells of a microorganism having an ability to asymmetrically hydrolyze ester bonds. The optically active α-substituted carboxylic acid derivatives and antipodes thereof provided by the invention are useful as raw materials for various liquid crystals and as synthetic intermediates for various optically active medicines or agricultural chemicals.

10 Claims, 8 Drawing Sheets

OPTICALLY ACTIVE α-SUBSTITUTED CARBOXYLIC ACID DERIVATIVES AND METHOD FOR PRODUCING THE SAME

TECHNICAL FIELD

The present invention relates to a method for producing optically active α-substituted carboxylic acid derivatives and antipodes thereof which are useful as raw materials for various liquid crystals and as synthetic intermediates for various optically active medicines or agricultural chemicals.

BACKGROUND ART

Of optically active α-substituted carboxylic acid derivatives, a method for producing, for example, an optically active α-methylhexanoic acid ester has been reported in which α-methylhexanoic acid is esterified stereoselectively using lipase (E. K. Heinz, Tetrahedron: Asymmetry, 2(3), 165 (1991)). However, this method is not satisfactory in terms of both yield and optical purity when industrial production is intended.

Of optically active α-substituted carboxylic acid derivatives, an optically active α-methylsuccinic acid monoester might possibly be obtained by partially hydrolyzing an optically active α-methylsuccinic acid diester using an alkali catalyst or the like. In this case, however, the reaction products are obtained as a mixture of α-methylsuccinic acid, α-methylsuccinic acid-1-monoester, α-methylsuccinic acid-4-monoester and α-methylsuccinic acid diester. Thus, it is difficult to obtain the product of interest selectively and at high purity. Furthermore, when a racemic mixture is used as a substrate, an ability to perform optical resolution cannot be expected from such a mode of reaction.

On the other hand, as a method for selectively synthesizing an α-methylsuccinic acid monoester, the method as described below using itaconic anhydride as a starting material is known in general (Barnett, Morris, Biochem. J., 40, 451 (1946)).

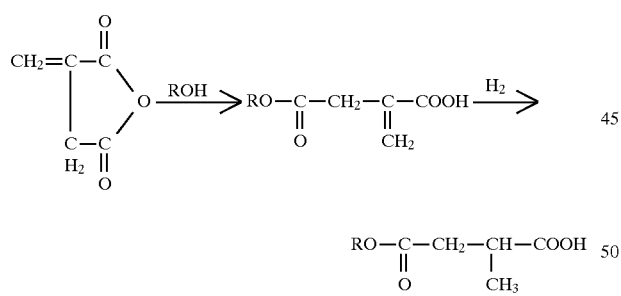

However, the α-methylsuccinic acid monoester obtained by the above method is a racemate and an optically active compound cannot be obtained in such a mode of reaction.

There has also been reported a method in which itaconic acid or dimethyl itaconate is asymmetrically reduced to thereby obtain optically active α-methylsuccinic acid or optically active dimethyl α-methylsuccinate. However, since this method needs an expensive asymmetric catalyst, it cannot be regarded as an industrially advantageous method (T. Morimoto et al., Chem., Pharm. Bull., 41(6), 1149 (1993)).

On the other hand, a method has been reported in which an α-methylsuccinic acid diester is hydrolyzed by porcine pancreatic lipase to thereby obtain α-methylsuccinic acid-1-monoester (Eryka Guibe-Jampel et al., J. Chem. Soc., Chem. Commun., 1080, 1987).

Although the optical purity and position selectivity of the ester obtained by this method are fairly high, it cannot be regarded as an industrially advantageous method since an expensive, animal-derived enzyme is used. Further, Japanese Unexamined Patent Publication No. 2-195890 discloses a method in which an α-methylsuccinic acid diester is hydrolyzed by a microorganism-derived enzyme to thereby obtains α-methylsuccinic acid-4-monoester. In this method, position selectivity is high with the ratio of 4-monoester in the resultant products being 95 –98%. However, stereoselective hydrolysis is hardly achieved. When a racemic diester is used as a starting material, the optical purity of the resultant products is only 16% e.e.

As methods for producing, for example, optically active β-hydroxyisobutyric acid derivatives out of optically active α-substituted carboxylic acid derivatives, there have been reported a method of asymmetric reduction of a β-keto acid ester, a method of optical resolution, a method of oxidation of 1,3-diol, a method of β-hydroxylation of fatty acid, a method of direct fermentation, and the like as a chemical method or a method using a microorganism. Of these method, a method of producing β-hydroxyisobutyric acid using the metabolic pathway of a microorganism is practiced in an industrial scale (Japanese Examined Patent Publications No. 59-21599, No. 59-21600, No. 60-16235, No. 61-12676, etc.). However, these methods using the metabolic pathway of a microorganism require a coenzyme regeneration system and ATP is indispensable as an energy source. Thus, in order to activate the metabolic system, it is necessary to culture the microorganism under aerobic conditions while supplying energy sources such as glucose. Therefore, these methods have the following problems. It takes a long time for cultivation; it is difficult to produce the product of interest at a high concentration; aseptic conditions are required; it is difficult to recycle cells; and the like.

By the way, of optically active α-substituted carboxylic acid derivatives, nothing has been known about, for example, optically active 2,5-dimethylhexanedioic acid derivatives and a method for producing the same.

Further, of optically active α-substituted carboxylic acid derivatives, nothing has been known about, for example, optically active 2-methyl-5-methylenehexanedioic acid derivatives and a method for producing the same.

DISCLOSURE OF THE INVENTION

It is an object of the invention to provide a novel, optically active α-substituted carboxylic acid derivative which is represented by the general formula (I) described below and which is expected to be useful as a synthetic intermediate for various optically active compounds. It is another object of the invention to provide a method for producing an optically active α-substituted carboxylic acid derivative, and an antipode thereof, which is represented by the general formula (I') described below that includes conventional, optically active α-substituted carboxylic acid derivatives.

The present invention includes the following inventions:

(1) An optically active α-substituted carboxylic acid derivative represented by the general formula (I):

$$R_1-(CH_2)_n-C^*H-\underset{\underset{O}{\|}}{\underset{|}{C}}-OR_2 \qquad \text{(I)}$$
$$\phantom{R_1-(CH_2)_n-}\overset{CH_3}{|}$$

(wherein $R_1$ is $$-\underset{\underset{CH_2}{\|}}{C}-COOR_2 \quad \text{or} \quad -\underset{\underset{CH_3}{|}}{CH}-COOR_2;$$

$R_2$ is a hydrogen atom or an alkyl group with 1–6 carbon atoms; n is an integer of 1 or 2; and * represents an asymmetric carbon atom).

(2) The compound as described in (1) above, which is an optically active dicarboxylic acid derivative represented by the general formula (Ia):

$$R_2O-\underset{\underset{O}{\|}}{C}-\underset{\underset{CH_3}{|}}{C^*H}-(CH_2)_2-\overset{CH_3}{\underset{|}{C^*H}}-\underset{\underset{O}{\|}}{C}-OR_2 \qquad \text{(Ia)}$$

(wherein $R_2$ is a hydrogen atom or an alkyl group with 1–6 carbon atoms; and * represents an asymmetric carbon atom).

(3) The compound as described in (1) above, which is an optically active, unsaturated dicarboxylic acid derivative represented by the general formula (Ib):

$$R_2O-\underset{\underset{O}{\|}}{C}-\underset{\underset{CH_2}{\|}}{C}-(CH_2)_2-\overset{CH_3}{\underset{|}{C^*H}}-\underset{\underset{O}{\|}}{C}-OH \qquad \text{(Ib)}$$

(wherein $R_2$ is a hydrogen atom or an alkyl group with 1–6 carbon atoms; and * represents an asymmetric carbon atom).

(4) The compound as described in (1) above, which is an optically active, unsaturated dicarboxylic acid derivative represented by the general formula (Ic):

$$R_2O-\underset{\underset{O}{\|}}{C}-\underset{\underset{CH_2}{\|}}{C}-(CH_2)_2-\overset{CH_3}{\underset{|}{C^*H}}-\underset{\underset{O}{\|}}{C}-OR_2 \qquad \text{(Ic)}$$

(wherein $R_2$ is a hydrogen atom or an alkyl group with 1–6 carbon atoms; and * represents an asymmetric carbon atom).

(5) A method for producing an optically active α-substituted carboxylic acid derivative represented by the general formula (I') below and an antipode thereof:

$$R_1'-(CH_2)_n-\overset{CH_3}{\underset{|}{C^*H}}-\underset{\underset{O}{\|}}{C}-OR_2 \qquad \text{(I')}$$

(wherein $R_1'$ is a hydrogen atom, a hydroxyl group, $$-\underset{\underset{CH_2}{\|}}{C}-COOR_2', \quad -\underset{\underset{CH_3}{|}}{CH}-COOR_2' \text{ or } -COOR_2';$$

n is an integer of 1 to 4; $R_2'$ is an alkyl group with 1–6 carbon atoms; $R_2$ is a hydrogen atom or an alkyl group with 1–6 carbon atoms; and * represents an asymmetric carbon atom), which method is characterized by allowing a culture, cells or a material obtainable from cells of a microorganism having an ability to asymmetrically hydrolyze ester bonds to act upon a racemic α-substituted carboxylic acid ester represented by the general formula (II):

$$R_1'-(CH_2)_n-\overset{CH_3}{\underset{|}{CH}}-\underset{\underset{O}{\|}}{C}-OR_2' \qquad \text{(II)}$$

(wherein $R_1'$, $R_2'$ and n are as defined above).

(6) The production method of (5) above, which is characterized by allowing a culture, cells or a material obtainable from cells of a microorganism having an ability to asymmetrically hydrolyze ester bonds to act upon a racemic, dicarboxylic acid diester represented by the general formula (IIa):

$$R_2'O-\underset{\underset{O}{\|}}{C}-\underset{\underset{CH_3}{|}}{CH}-(CH_2)_2-\overset{CH_3}{\underset{|}{CH}}-\underset{\underset{O}{\|}}{C}-OR_2' \qquad \text{(IIa)}$$

(wherein $R_2'$ is an alkyl group with 1–6 carbon atoms) to thereby obtain an optically active dicarboxylic acid represented by the general formula (Ia'):

$$HO-\underset{\underset{O}{\|}}{C}-\underset{\underset{CH_3}{|}}{C^*H}-(CH_2)_2-\overset{CH_3}{\underset{|}{C^*H}}-\underset{\underset{O}{\|}}{C}-OH \qquad \text{(Ia')}$$

(wherein * represents an asymmetric carbon atom)
and/or an antipodal diester thereof represented by the general formula (Ia"):

$$R_2'O-\underset{\underset{O}{\|}}{C}-\underset{\underset{CH_3}{|}}{C^*H}-(CH_2)_2-\overset{CH_3}{\underset{|}{C^*H}}-\underset{\underset{O}{\|}}{C}-OR_2' \qquad \text{(Ia")}$$

(wherein $R_2'$ is as defined above, and * represents an asymmetric carbon atom).

(7) The production method of (5) above, which is characterized by allowing a culture, cells or a material obtainable from cells of a microorganism having an ability to asymmetrically hydrolyze ester bonds to act upon a racemic α-methylalkanoic acid ester represented by the general formula (IId):

$$CH_3(CH_2)_n-\overset{CH_3}{\underset{|}{CH}}-\underset{\underset{O}{\|}}{C}-OR_2' \qquad \text{(IId)}$$

(wherein $R_2'$ is an alkyl group with 1–6 carbon atoms, and n is an integer of 1 to 3)
to thereby obtain an optically active α-methylalkanoic acid represented by the general formula (Id'):

$$CH_3(CH_2)_n-\overset{CH_3}{\underset{|}{C^*H}}-\underset{\underset{O}{\|}}{C}-OH \qquad \text{(Id')}$$

(wherein n is as defined above, and * represents an asymmetric carbon atom)
and/or an antipodal ester thereof represented by the general formula (Id"):

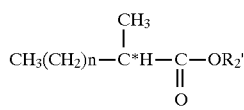

(wherein $R_2'$ and n are as defined above, and * represents an asymmetric carbon atom).

(8) The production method of (5) above, which is characterized by allowing a culture, cells or a material obtainable from cells of a microorganism having an ability to asymmetrically hydrolyze ester bonds to act upon a racemic, unsaturated dicarboxylic acid diester represented by the general formula (IIb):

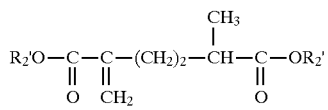

(wherein $R_2'$ is an alkyl group with 1–6 carbon atoms) to thereby obtain an optically active, unsaturated dicarboxylic acid monoester represented by the general formula (Ib'):

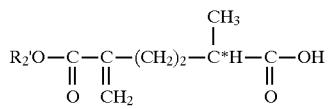

(wherein $R_2'$ is as defined above, and * represents an asymmetric carbon atom)
and/or an antipodal ester thereof represented by the general formula (Ic'):

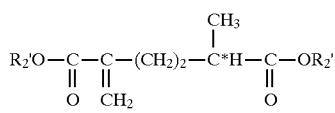

(wherein $R_2'$) is as defined above, and * represents an asymmetric carbon atom).

(9) The production method of (5) above, which is characterized by allowing a culture, cells or a material obtainable from cells of a microorganism having an ability to asymmetrically hydrolyze ester bonds to act upon a racemic α-methylalkanedicarboxylic acid diester represented by the general formula (IIe):

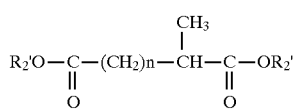

(wherein $R_2'$ is an alkyl group with 1–6 carbon atoms, and n is an integer of 1 or 2)
to thereby obtain an optically active α-methylalkanedicarboxylic acid-ω-monoester represented by the general formula (Ie'):

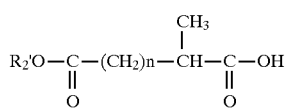

(wherein $R_2'$ and n are as defined above, and * represents an asymmetric carbon atom)
and/or an antipodal diester thereof represented by the general formula (Ie"):

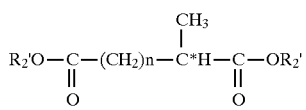

(wherein $R_2'$ and n are as defined above, and * represents an asymmetric carbon atom).

(10) The production method of (5) above, which is characterized by allowing a culture, cells or a material obtainable from cells of a microorganism having an ability to asymmetrically hydrolyze ester bonds to act upon a racemic β-hydroxycarboxylic acid ester to thereby obtain an optically active β-hydroxycarboxylic acid and/or an antipodal ester thereof.

(11) The production method described in any one of (5) through (10) above, wherein the microorganism having an ability to asymmetrically hydrolyze ester bonds is a microorganism having an ability to produce lipase, protease or esterase.

(12) The production method described in any one of (5) through (10) above, wherein the microorganism having an ability to asymmetrically hydrolyze ester bonds is a microorganism belonging to the genus Pseudomonas or the genus Escherichia.

(13) The production method described in any one of (5) through (10) above, wherein the microorganism having an ability to asymmetrically hydrolyze ester bonds is a genetically engineered microorganism which has been transformed with a gene coding for an enzyme that asymmetrically hydrolyzes ester bonds.

As examples of the alkyl group with 1–6 carbon atoms represented by $R_3$ or $R_3'$ in the above formulas, a methyl group, ethyl group, propyl group, isopropyl group, butyl group, isobutyl group, sec-butyl group, t-butyl group, pentyl group, hexyl group and the like may be enumerated.

The microorganism used in the invention is not particularly limited. Any microorganism may be used as long as it has an ability to asymmetrically hydrolyze ester bonds of a racemic α-substituted carboxylic acid ester to produce an optically active α-substituted carboxylic acid and an antipode thereof. Typical examples of such a microorganism include microorganisms belonging to the genus Pseudomonas or Escherichia. Specifically, *Pseudomonas putida* MR-2068 (FERM BP-3846) and *Escherichia coli* MR-2103 (FERM BP-3835) may be enumerated. *Escherichia coli* MR-2103 (FERM BP-3835) is a strain which has been transformed with an esterase gene derived from *Pseudomonas putida* MR-2068 (FERM BP-3846).

The cultivation of the microorganism used in the invention may be performed on either a liquid medium or a solid medium. As a medium for cultivation, a medium appropriately containing carbon sources and nitrogen sources which microorganisms usually can assimilate and components such as vitamins and minerals may be used. In order to improve the ability of hydrolysis of the microorganism, a small amount of an ester may be added to the medium. The cultivation is carried out at a temperature and a pH under which the microorganism can grow. It is preferable to carry out the cultivation under the optimum conditions for the strain to be used. In order to promote the growth of the microorganism, aeration agitation may be carried out.

When a hydrolysis reaction is carried out, an ester may be added to the medium at the beginning of, or during the cultivation. Or, an ester may be added to the culture solution after the microorganism has been grown. Alternatively, cells of the microorganism grown may be harvested by centrifuge or the like and then added to the reaction medium containing an ester. As cells used in the invention, those treated with acetone, toluene or the like may be used.

Instead of cells per se, a culture (such as a culture solution) or a material obtainable from cells (such as disrupted cells, a cell extract, a crude enzyme, a purified enzyme) may be used. Further, it is also possible to immobilize a microorganism or an enzyme on an appropriate carrier and to recover and recycle the microorganism or the enzyme after the reaction. As an enzyme for the above purpose, various lipases, proteases and esterases derived from microorganisms may be used.

As a reaction medium, for example, an ion-exchanged water or a buffer may be used. The ester concentration in the reaction medium or the culture solution is preferably 0.1–70% by weight, more preferably 5–40% by weight. It is also possible to add methanol, acetone, surfactants and the like to the reaction system. The pH of the reaction solution is 2–11, preferably 5–8. As the reaction proceeds, the pH of the reaction solution decreases due to the resultant carboxylic acid. When such a decrease occurs, it is desirable to maintain the optimum pH with an appropriate neutralizer. The reaction temperature is preferably 5°–70° C., more preferably 10°–60° C.

After the completion of the reaction, the separation and purification of products from the reaction solution may be performed by extraction with organic solvents such as ethyl acetate, chloroform and ether, or by application of a conventional technique such as distillation and column chromatography. As a result, an optically active α-substituted carboxylic acid ester can be purified and obtained. The optically active α-substituted carboxylic acid which is an antipode of the above-described ester can be recovered as follows. By lowering the pH of the aqueous phase after the extraction to 2 or below, the acid is made into a free acid and then extracted using an organic solvent such as ethyl acetate.

An optically active α-substituted carboxylic acid ester obtained by the procedures described above can be converted into an optically active α-substituted carboxylic acid with its configuration being maintained by hydrolyzing the ester in a conventional manner under conditions where racemization would not occur. Also, an optically active α-substituted carboxylic acid can be converted into an optically active α-substituted carboxylic acid ester with its configuration being maintained by esterifying the acid in a conventional manner under conditions where racemization would not occur.

BEST MODES FOR CARRYING OUT THE INVENTION

Hereinbelow, the present invention will be described in more detail with reference to the following Examples, which should not be construed as limiting the scope of the present invention.

(Example 1)

Production of (S)-Methyl 2-Chloro-3-Hydroxypropionate

*Escherichia coli* MR-2103 (FERM BP-3835) was seeded on 50 ml of LB medium (1% polypeptone, 0.5% yeast extract, 0.5% NaCl) containing 50 μg/ml ampicillin and cultured at 37° C. for 20 hours under shaking. After the completion of the cultivation, the culture solution was centrifuged. The total volume of the cells harvested were washed with ion-exchanged water and then suspended in 50 ml of 50 mM phosphate buffer (pH 7.0). To this cell suspension, 5 g of racemic methyl 2-chloro-3-hydroxypropionate was added and reacted at 30° C. for 20 hours. During the reaction, the pH of the reaction solution was adjusted at 7.0 using 1N NaOH aqueous solution. After the completion of the reaction, cells were removed by centrifugation and unreacted methyl 2-chloro-3-hydroxypropionate was extracted with ethyl acetate. The organic layer was dehydrated by adding thereto anhydrous sodium sulfate and the solvent was removed by evaporation. The organic layer was further distilled and purified to thereby obtain an ester fraction of 0.65 g.

(Example 2)

An experiment was conducted in the same manner as described in Example 1 except that the reaction temperature was 15° C. As a result, an ester fraction of 0.85 g was obtained.

(Example 3)

An experiment was conducted in the same manner as described in Example 1 except that the reaction temperature was 15° C. and that 5% calcium hydroxide suspension was used as a neutralizer. As a result, an ester fraction of 1.1 g was obtained.

(Example 4)

An experiment was conducted in the same manner as described in example 1 except that the reaction temperature was 15° C and that 5% magnesium hydroxide suspension was used as a neutralizer. As a result, an ester fraction of 1.3 g was obtained.

(Example 5)

An experiment was conducted in the same manner as described in Example 1 except that the reaction temperature was 15° C. and that 14% aqueous ammonia was used as a neutralizer. As a result, an ester fraction of 1.7 g was obtained. The results of Examples 1–5 are summarized in Table 1.

TABLE 1

| Example | Amount of Production (g) | Yield (%) | Optical Purity (% e.e.) |
|---|---|---|---|
| 1 | 0.65 | 26 | >99 |
| 2 | 0.85 | 34 | >99 |
| 3 | 1.1 | 44 | >99 |
| 4 | 1.3 | 52 | >99 |
| 5 | 1.7 | 68 | >99 |

Shown below are the physical property data for the ester fraction obtained in example 5.

Figure 1:
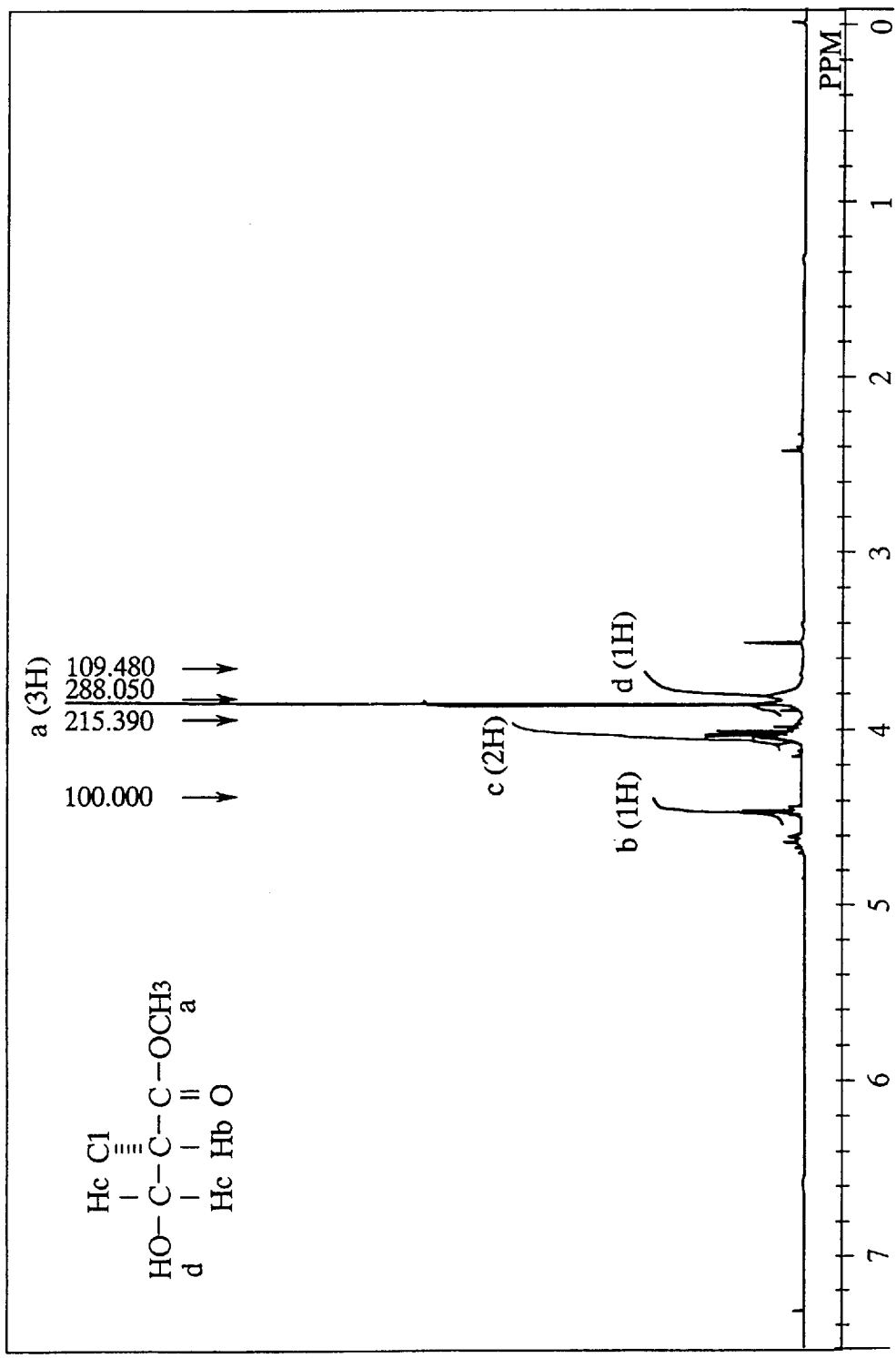
FIG. 1 shows the 1H-NMR spectrum of the (S)-methyl 2-chloro-3-hydroxypropionate obtained in Example 5.

| <¹H-NMR spectrum> CDCl₃ | Internal Standard TMS (FIG. 1) |
|---|---|
| $\delta_H$ 3.79 | (1H, s, —OH) |
| $\delta_H$ 3.83 | (3H, s, —CH₃) |
| $\delta_H$ 3.98~4.03 | (2H, m, —CH₂—) |
| $\delta_H$ 4.41~4.44 | (1H, t, —CH—) |

Figure 2:
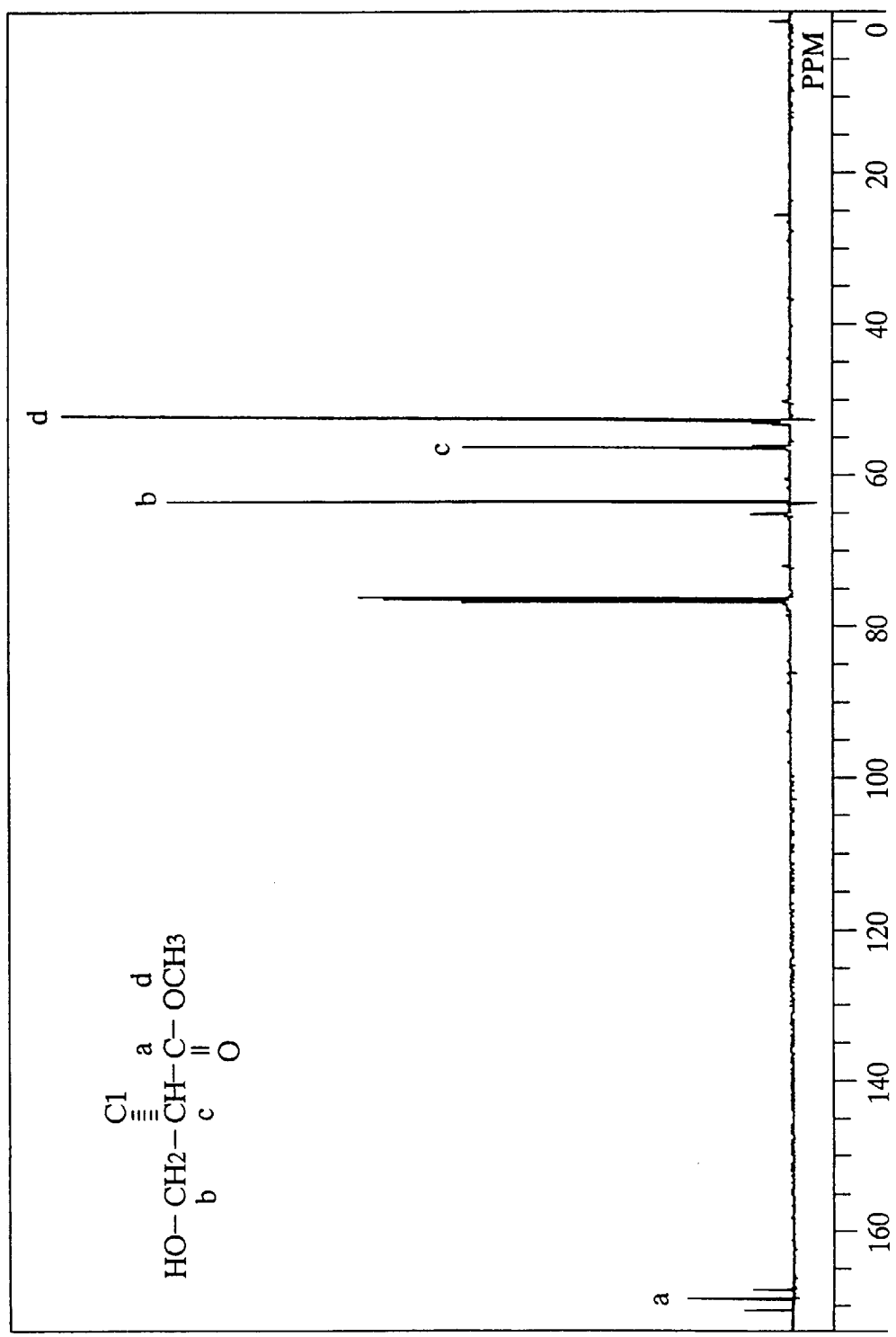
FIG. 2 shows the $^{13}$C-NMR spectrum of the same compound.

| <¹³C-NMR spectrum> CDCl₃ | Internal Standard TMS (FIG. 2) |
|---|---|
| $\delta_c$ 53.31 | (—CH₃) |
| $\delta_c$ 56.88 | (—CH—) |
| $\delta_c$ 64.14 | (—CH₂—) |
| $\delta_c$ 169.08 | (C=O) |

<Specific Rotation>
$[\alpha]^{25}_D = -6.74°$ (neat)
<Optical Purity>
(S)-form 100% e.e.
Determined by ¹H-NMR in the presence of tris[3-(heptafluoro-propylhydroxymethylene)-(+)-camphorato]europium(III).

(Example 6)
Production of (2S,5S)-Dimethylhexanedioic Acid Dimethyl Ester

*Escherichia coli* MR-2103 (FERM BP-3835) was seeded on 500 ml of LB medium (1% polypeptone, 0.5% yeast extract, 0.5% NaCl) containing 50μg/ml ampicillin and cultured at 37° C. for 20 hours under shaking. After the completion of the cultivation, the culture solution was centrifuged. The total volume of the cells harvested were washed with ion-exchanged water and then suspended in 500 ml of 50 mM phosphate buffer (pH 7.0). To this cell suspension, 50 g of racemic 2, 5-dimethylhexanedioic acid dimethyl ester was added and reacted at 30° C. for 20 hours. During the reaction, the pH of the reaction solution was adjusted at 7.0 using 1N NaOH aqueous solution. After the completion of the reaction, cells were removed by centrifugation and unreacted 2,5-dimethylhexanedioic acid dimethyl ester was extracted with ethyl acetate. The organic layer was dehydrated by adding thereto anhydrous sodium sulfate and the solvent was removed by evaporation. The organic layer was further distilled and purified to thereby obtain a diester fraction of 9.6 g.

Shown below are the physical property data for the thus obtained diester fraction.
(2S,5S)-dimethylhexanedioic acid dimethyl ester

Figure 3:
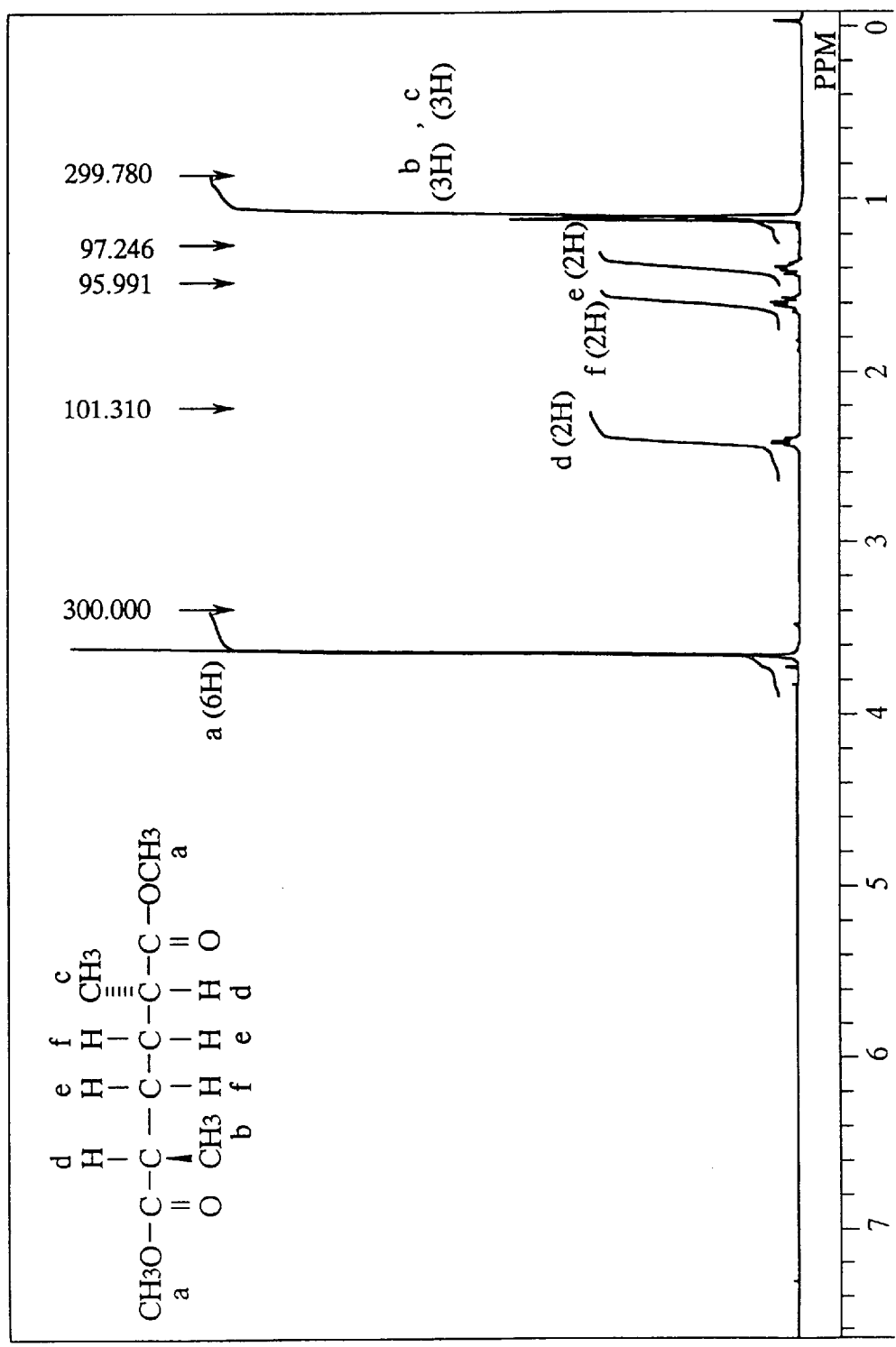
FIG. 3 shows the $^1$H-NMR spectrum of the (2S,5S)-dimethylhexanedioic acid dimethyl ester obtained in Example 6.

| <¹H-NMR spectrum> CDCl₃ | Internal Standard TMS (FIG. 3) |
|---|---|
| $\delta_H$ 1.14~1.16 | (6H, d, —CH₃) |
| $\delta_H$ 1.43~1.45 | (2H, m, —CH₂—) |
| $\delta_H$ 1.63~1.66 | (2H, m, —CH₂—) |
| $\delta_H$ 2.43~2.45 | (2H, q, —CH—) |
| $\delta_H$ 3.68 | (6H, s, —COOCH₃) |

Figure 4:
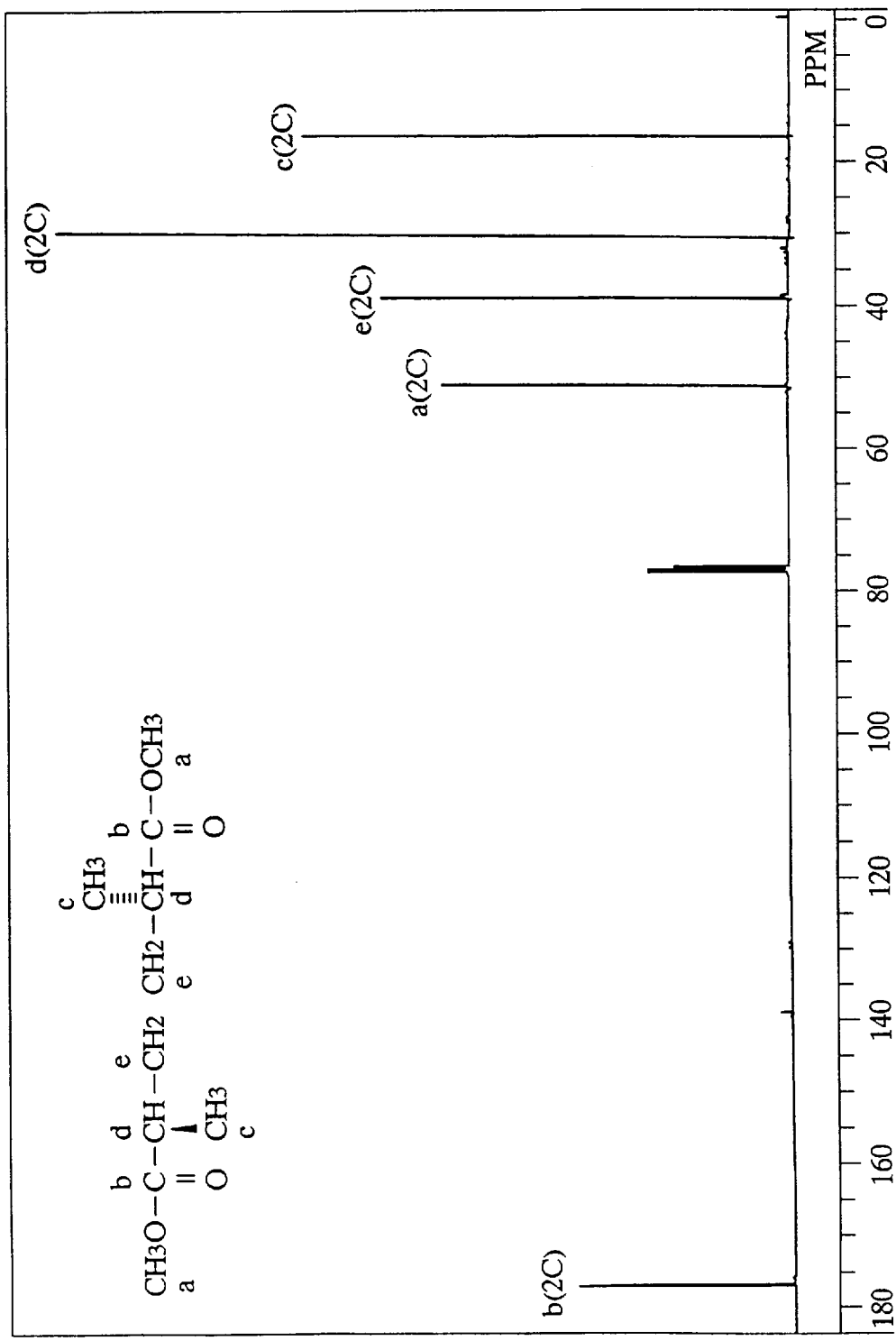
FIG. 4 shows the $^{13}$C-NMR spectrum of the same compound.

| <¹³C-NMR spectrum> CDCl₃ | Internal Standard TMS (FIG. 4) |
|---|---|
| $\delta_c$ 16.98 | (—CH₃) |
| $\delta_c$ 31.18 | (—CH—) |
| $\delta_c$ 39.31 | (—CH₂—) |
| $\delta_c$ 51.77 | (—COOCH₃) |
| $\delta_c$ 176.83 | (C=O) |

<Specific Rotation>
$[\alpha]^{25}_D = +28.8°$ (neat)

(Example 7)
Production of Optically Active α-Methylhexanoic Acid and an Antipodal Ester Thereof

*Escherichia coli* MR-2103 (FERM BP-3835) was seeded on 50 ml of LB medium (1% polypeptone, 0.5% yeast extract, 0.5% NaCl) containing 50 μg/ml ampicillin and cultured at 37° C. for 20 hours under shaking. After the completion of the cultivation, the culture solution was centrifuged. The total volume of the cells harvested were washed with ion-exchanged water and then suspended in 50 ml of 50 mM phosphate buffer (pH 7.0). To this cell suspension, 5 g of racemic methyl α-methylhexanoate was added and reacted at 30° C. for 20 hours. During the reaction, the pH of the reaction solution was adjusted at 7.0 using in NaOH aqueous solution. After the completion of the reaction, cells were removed by centrifugation and unreacted methyl α-methylhexanoate was extracted with ethyl acetate. The organic layer was dehydrated by adding thereto anhydrous sodium sulfate and the solvent was removed by evaporation. The organic layer was further distilled and purified to thereby obtain 1.9 g of optically active methyl α-methylhexanoate. The specific rotation of this optically active methyl α-methylhexanoate was measured and found to be $[\alpha]^{25}_D=+16.3$. Then, after the pH of the aqueous layer was lowered to 2.0 with dilute sulfuric acid, the acid in the aqueous layer was extracted with ethyl acetate. The organic layer was dehydrated by adding thereto anhydrous sodium sulfate and the solvent was removed by evaporation. The organic layer was further distilled and purified to thereby obtain 1.3 g of optically active α-methylhexanoic acid. The specific rotation of this sample was measured and found to be $[\alpha]25_D=-16.3$.

(Example 8)

Production of (S)-2-Methyl-5-Methylenehexanedioic Acid Dimethyl Ester and (R)-2-Methyl-5-Methylenehexanedioic Acid-6-Monomethyl Ester

*Escherichia coli* MR-2103 (FERM BP-3835) was seeded on 500 ml of LB medium (1% polypeptone, 0.5% yeast extract, 0.5% NaCl) containing 50 μg/ml ampicillin and cultured at 37° C. for 20 hours under shaking. After the completion of the cultivation, the culture solution was centrifuged. The total volume of the cells harvested were washed with ion-exchanged water and then suspended in 500 ml of 50 mM phosphate buffer (pH 7.0). To this cell suspension, 50 g of racemic 2-methyl-5-methylenehexanedioic acid dimethyl ester was added and reacted at 30° C. for 20 hours. During the reaction, the pH of the reaction solution was adjusted at 7.0 using 1N NaOH aqueous solution. After the completion of the reaction, cells were removed by centrifugation and unreacted 2-methyl-5-methylenehexanedioic acid dimethyl ester was extracted with ethyl acetate. The organic layer was dehydrated by adding thereto anhydrous sodium sulfate and the solvent was removed by evaporation. The organic layer was further distilled and purified to thereby obtain a diester fraction of 17.6 g.

The pH of the aqueous layer after the extraction was lowered to 2.0 with dilute sulfuric acid, and then the acid in the aqueous layer was extracted with ethyl acetate. The organic layer was dehydrated by adding thereto anhydrous sodium sulfate and the solvent was removed by evaporation. The organic layer was further distilled and purified to thereby obtain 14.4 g of 2-methyl-5-methylenehexanedioic acid-6-monomethyl ester.

Shown below are the physical property data for each of the components obtained.

(1) (S)-2-Methyl-5-Methylenehexanedioic Acid Dimethyl Ester

Figure 5:
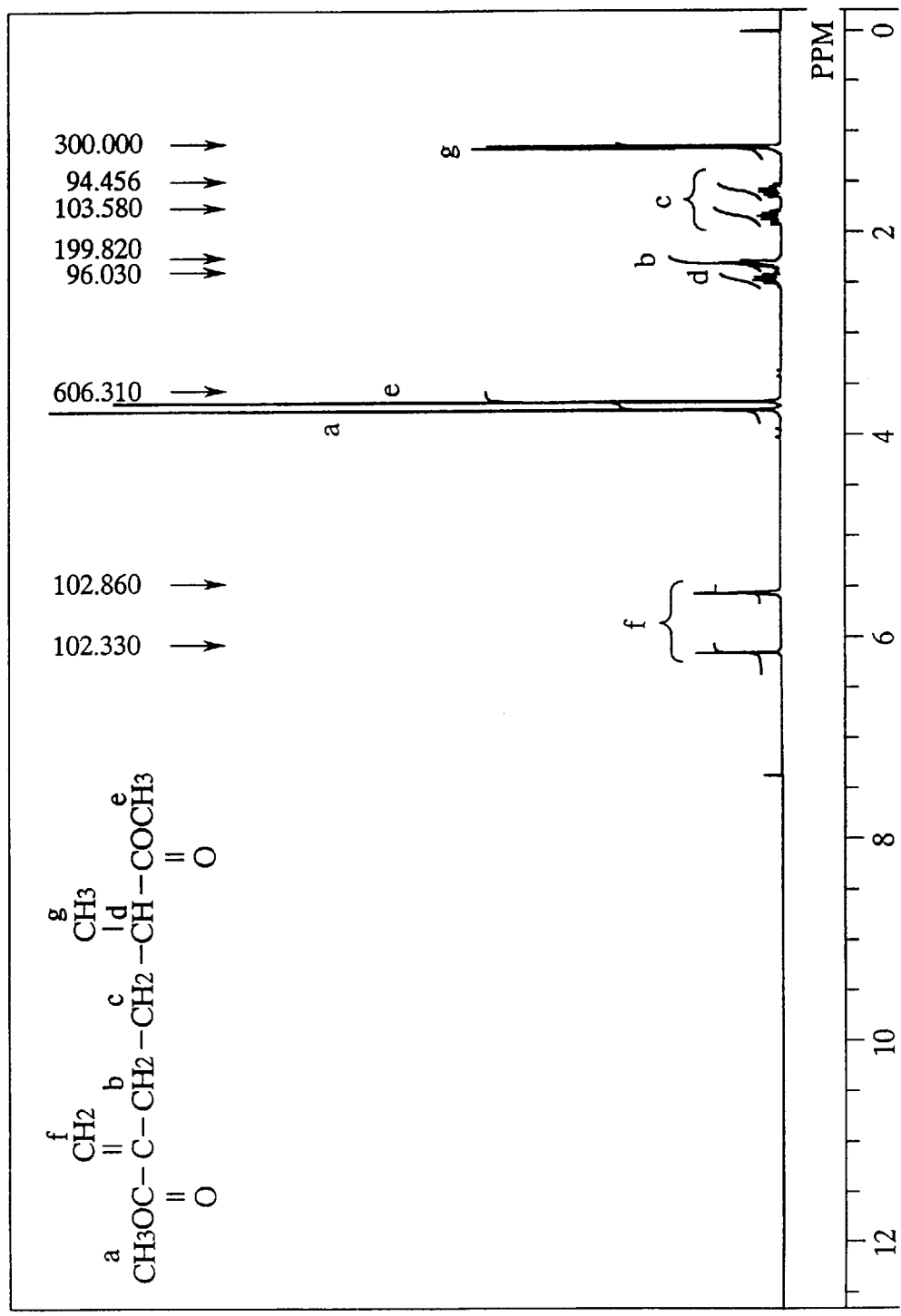
FIG. 5 shows the $^1$H-NMR spectrum of the (S)-2-methyl-5-methylenehexanedioic acid dimethyl ester obtained in Example 8.

| <$^1$H-NMR spectrum> CDCl$_3$ | Internal Standard TMS (FIG. 5) |
|---|---|
| $\delta_H$ 1.17~1.20 | (3H, d, —CH$_3$) |
| $\delta_H$ 1.50~2.00 | (2H, m, —CH$_2$—) |
| $\delta_H$ 2.20~2.35 | (2H, t, —CH$_2$—) |
| $\delta_H$ 2.40~2.55 | (1H, m, —CH—) |
| $\delta_H$ 3.68 | (3H, s, —COOCH$_3$) |
| $\delta_H$ 3.75 | (3H, s, —COOCH$_3$) |
| $\delta_H$ 5.56, 6.16 | (2H, s, CH$_2$=) |

Figure 6:
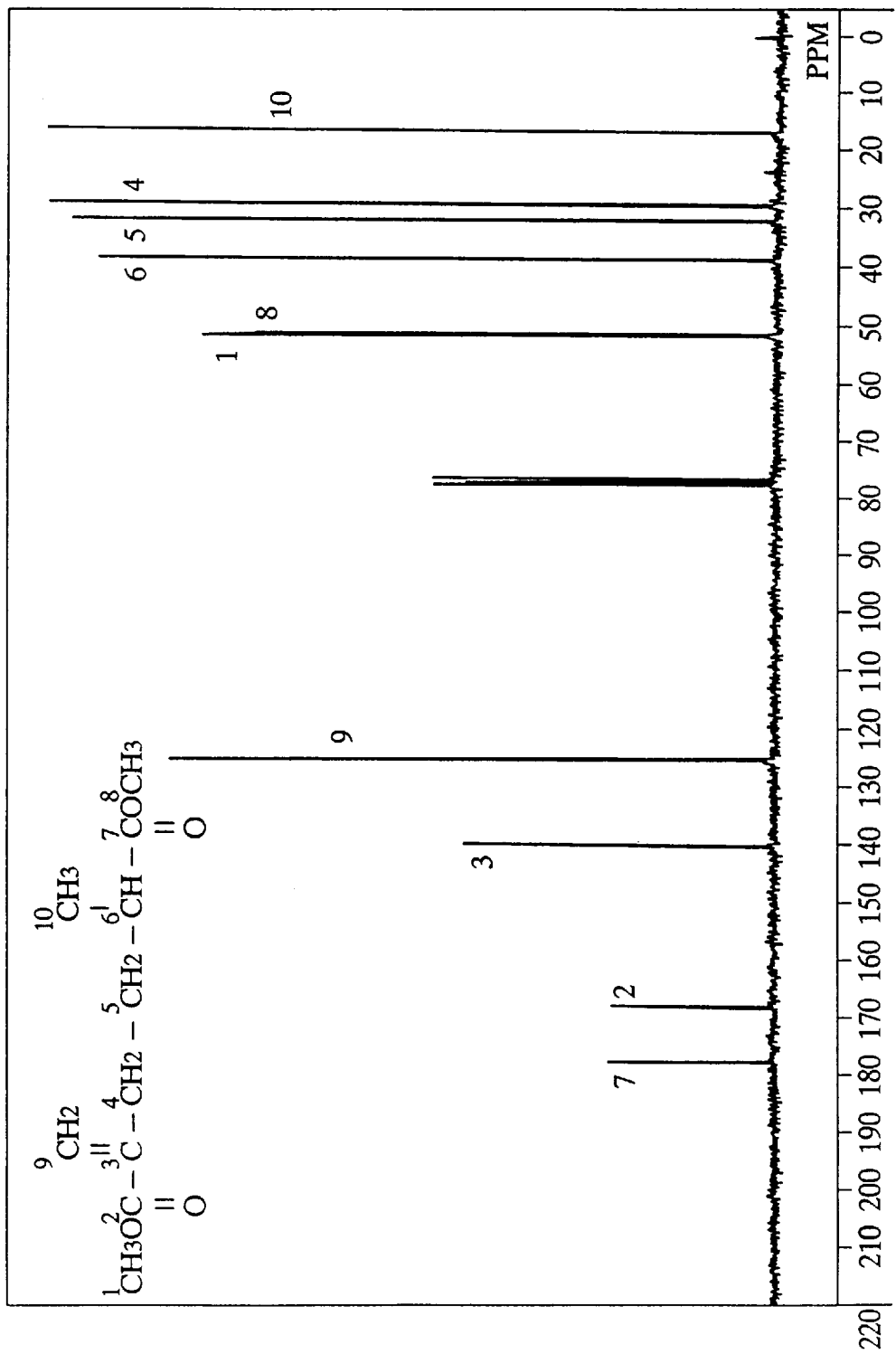
FIG. 6 shows the $^{13}$C-NMR spectrum of the same compound.

| <$^{13}$C-NMR spectrum> CDCl$_3$ | Internal Standard TMS (FIG. 6) |
|---|---|
| $\delta_c$ 17.12 | (—CH$_3$) |
| $\delta_c$ 29.59 | (—CH$_2$—) |
| $\delta_c$ 32.30 | (—CH$_2$—) |
| $\delta_c$ 38.95 | (—CH—) |
| $\delta_c$ 51.57, 51.84 | (—COOCH$_3$) |
| $\delta_c$ 125.42 | (CH$_2$=) |
| $\delta_c$ 139.87 | (—C=) |
| $\delta_c$ 167.49 | (C=O) |
| $\delta_c$ 176.88 | (C=O) |

<Specific Rotation>
$[\alpha]^{25}_D = +16.0°$ (c = 2.0, CHCl$_3$)
<Optical Purity>
(S)-form 100% e.e.
Determined by $^1$H-NMR in the presence of tris[3-(heptafluoropropylhydroxymethylene)-(+)-camphorato]europium(III).

(2) (R)-2-Methyl-5-Methylenehexanedioic Acid-6-Monomethyl Ester

Figure 7:
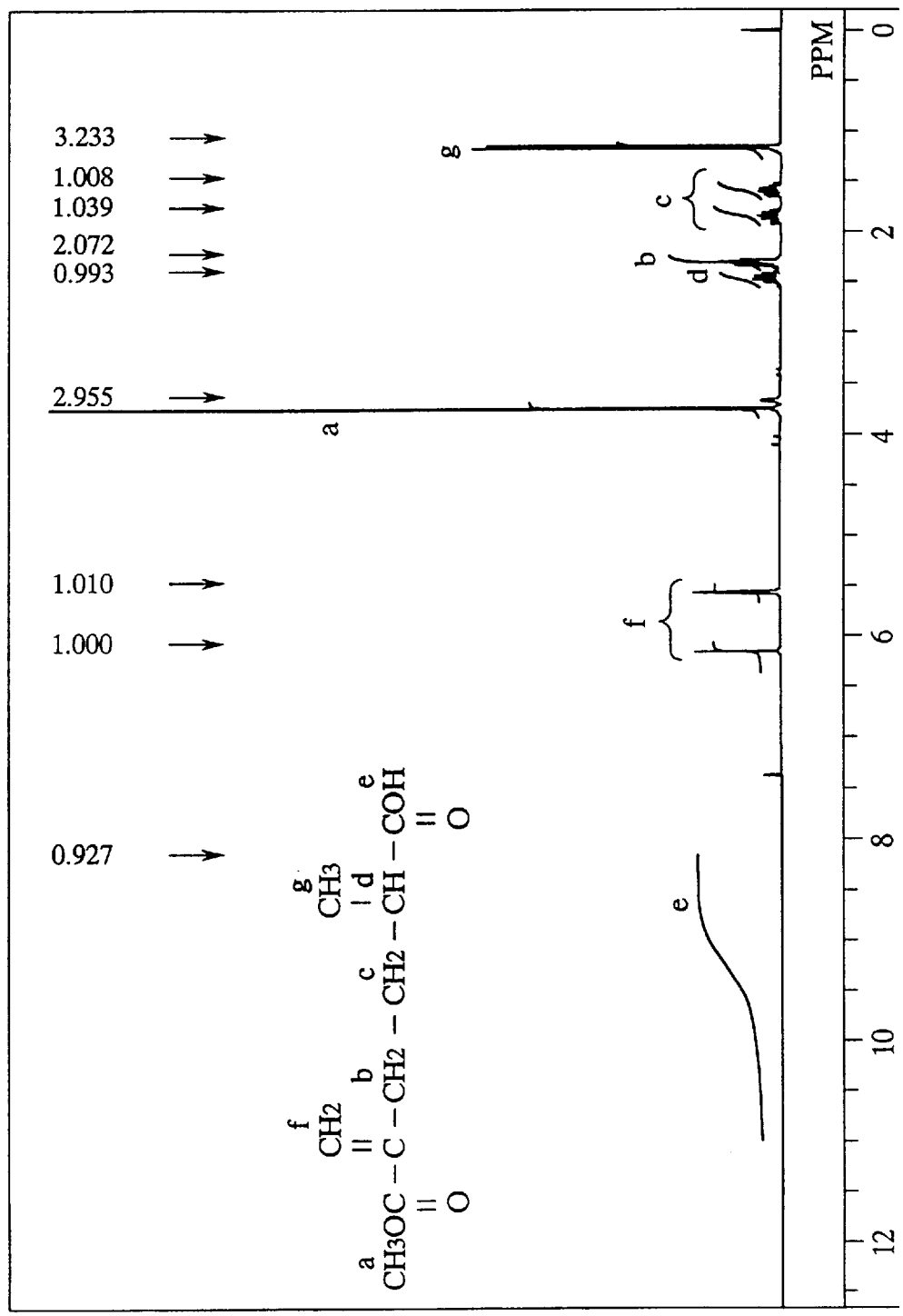
FIG. 7 shows the $^1$H-NMR spectrum of the (R)-2-methyl-5-methylenehexanedioic acid-6-monomethyl ester obtained in Example 8.

| <$^1$H-NMR spectrum> CDCl$_3$ | Internal Standard TMS (FIG. 7) |
|---|---|
| $\delta_H$ 1.21~1.26 | (3H, d, —CH$_3$) |
| $\delta_H$ 1.60~1.93 | (2H, m, —CH$_2$—) |
| $\delta_H$ 2.34~2.40 | (2H, t, —CH$_2$—) |
| $\delta_H$ 2.46~2.54 | (1H, m, —CH—) |
| $\delta_H$ 3.76 | (3H, s, —COOCH$_3$) |
| $\delta_H$ 5.59, 6.18 | (2H, s, CH$_2$=) |
| $\delta_H$ 8.00~10.00 | (1H, br, —COOH) |

Figure 8:
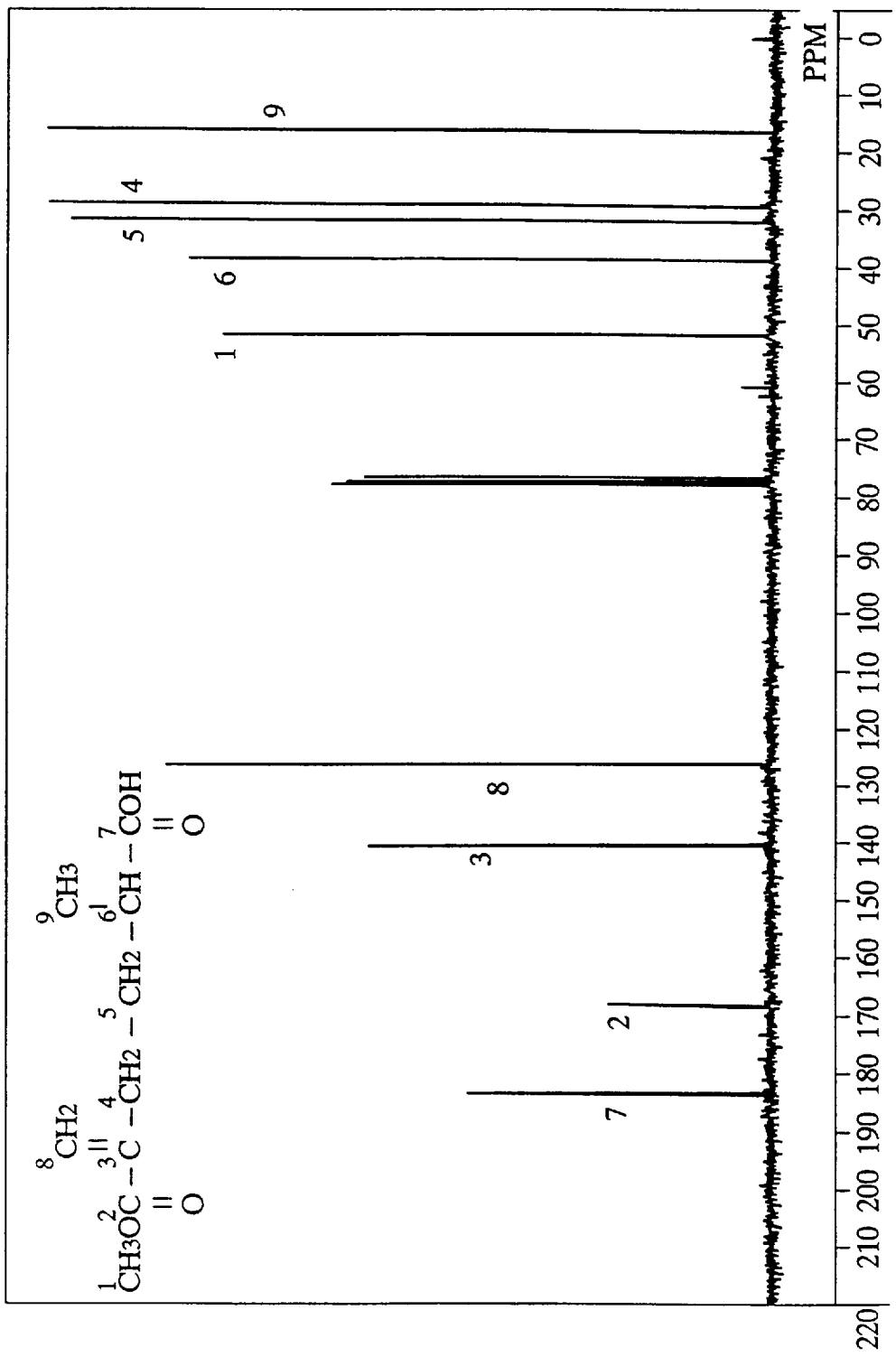
FIG. 8 shows the $^{13}$C-NMR spectrum of the same compound.

| <$^{13}$C-NMR spectrum> CDCl$_3$ | Internal Standard TMS (FIG. 8) |
|---|---|
| $\delta_c$ 17.08 | (—CH$_3$) |
| $\delta_c$ 29.50 | (—CH$_2$—) |
| $\delta_c$ 32.02 | (—CH$_2$—) |
| $\delta_c$ 38.84 | (—CH—) |
| $\delta_c$ 51.91 | (—COOCH$_3$) |
| $\delta_c$ 125.47 | (CH$_2$=) |
| $\delta_c$ 139.72 | (—C=) |
| $\delta_c$ 167.58 | (C=O) |
| $\delta_c$ 182.72 | (C=O) |

<Specific Rotation>
$[\alpha]^{25}_D = -10.4°$ )c = 2.0, CHCl$_3$)
<Optical Purity>
(R)-form 100% e.e.
Determined nu $^1$H-NMR in the presence of tris[3-(heptafluoropropylhydroxymethylee)-(+)-camphorato]europium(III) after conversion into the diester form.

(Example 9)
Production of an Optically Active Methylsuccinic Acid Monoester and an Antipodal Diester Thereof

*Escherichia coli* MR-2103 (FERM BP-3835) was seeded on 500 ml of LB medium (1% polypeptone, 0.5% yeast extract, 0.5% NaCl) containing 50 μg/ml ampicillin and cultured at 37° C. for 20 hours under shaking. After the completion of the cultivation, the culture solution was centrifuged. The total volume of the cells harvested were washed with ion-exchanged water and then suspended in 500 ml of 50 mM phosphate buffer (pH 7.0). To this cell suspension, 50 g of racemic dimethyl α-methylsuccinate was added and reacted at 30° C. for 20 hours. During the reaction, the pH of the reaction solution was adjusted at 7.0 using 10% NaOH aqueous solution. After the completion of the reaction, cells were removed by centrifugation and unreacted dimethyl α-methylsuccinate was extracted with ethyl acetate. The organic layer was dehydrated by adding thereto anhydrous sodium sulfate and the solvent was removed by evaporation. The organic layer was further distilled and purified to thereby obtain 19.8 g of optically active dimethyl α-methylsuccinate. The optical purity of this optically active dimethyl α-methylsuccinate was measured using an optical resolution column (Chiralcell OD; Daicel Chemical Industries, Ltd.) and found to be 99% e.e. in (S)-form. Then, after the pH of the aqueous layer was lowered to 2.0 with dilute sulfuric acid, the acid in the aqueous layer was extracted with ethyl acetate. The organic layer was dehydrated by adding thereto anhydrous sodium sulfate and the solvent was removed by evaporation. The organic layer was further distilled and purified to thereby obtain 17.2 g of optically active α-methylsuccinic acid-4-monoester. The optical purity of this compound was measured using an optical resolution column (Chiralcell OD; Daicel Chemical Industries, Ltd.) and found to be 96% e.e. in (R)-form. Further, from the $^1$H-NMR spectrum, the obtained monoester was only 4-ester, and the presence of 1-ester mixed was not observed.

(Example 10)
Production of an Optically Active α-Methylglutaric Acid Monoester and an Antipodal Diester Thereof To a cell suspension prepared in substantially the same manner as described in Example 9, 50 g of racemic dimethyl α-methylglutarate was added and reacted at 30° C. for 20 hours. During the reaction, the pH of the reaction solution was adjusted at 7.0 using 10% NaOH aqueous solution. After the completion of the reaction, cells were removed by centrifugation and unreacted dimethyl α-methylglutarate was extracted with ethyl acetate. The organic layer was dehydrated by adding thereto anhydrous sodium sulfate and the solvent was removed by evaporation. The organic layer was further distilled and purified to thereby obtain 18.2 g of optically active dimethyl α-methylglutarate. The optical purity of this optically active dimethyl α-methylglutarate was determined by $^1$H-NMR spectrum using tris [3-(heptafluoropropylhydroxymethylene)-(+)-camphorato]europium(II-I) and found to be 100% e.e. in (S)-form. Then, after the pH of the aqueous layer was lowered to 2.0 with dilute sulfuric acid, the acid in the aqueous layer was extracted with ethyl acetate. The organic layer was dehydrated by adding thereto anhydrous sodium sulfate and the solvent was removed by evaporation. The organic layer was further distilled and purified to thereby obtain 18.0 g of optically active α-methylglutaric acid-4-monoester. From the 1H-NMR spectrum, the obtained monoester was only 4-ester, and the presence of 1-ester mixed was not observed. After this optically active α-methylglutaric acid-4-monoester was converted into a corresponding diester according to conventional methods, the optical purity was determined as described above and found to be 96% e.e. in (R)-form.

(Example 11)

Production of Optically Active β-Hydroxyisobutyric Acid and an Antipodal Ester Thereof To a cell suspension prepared in substantially the same manner as described in Example 1, 5 g of racemic methyl β-hydroxyisobutyrate was added and reacted at 30° C. for 24 hours. During the reaction, the pH of the reaction solution was adjusted at 7.0 using 10% NaOH aqueous solution. After the completion of the reaction, cells were removed by centrifugation and unreacted methyl β-hydroxyisobutyrate was extracted with ethyl acetate. The organic layer was dehydrated by adding thereto anhydrous sodium sulfate and the solvent was removed by evaporation. The organic layer was further distilled and purified to thereby obtain 2.2 g of optically active methyl β-hydroxyisobutyrate. The specific rotation of this optically active methyl β-hydroxyisobutyrate was determined and found to be $[\alpha]^{25}_D=+24.9°$ (c=2.0, MeOH). Then, after the pH of the aqueous layer was lowered to 2.0 with dilute sulfuric acid, the acid in the aqueous layer was extracted with ethyl acetate. The organic layer was dehydrated by adding thereto anhydrous sodium sulfate and the solvent was removed by evaporation, to thereby obtain 2.0 g of optically active β-hydroxyisobutyric acid. The specific rotation of this optically active β-hydroxyisobutyric acid was determined and found to be $[\alpha]^{25}_D=-17.2°$ (c=2.0, MeOH).

Industrial Applicability

The optically active α-substituted carboxylic acid derivatives and antipodes thereof provided by the invention are useful as raw materials for various liquid crystals and as synthetic intermediates for various optically active medicines or agricultural chemicals.

We claim:

1. An optically active α-substituted carboxylic acid derivative represented by the general formula (I):

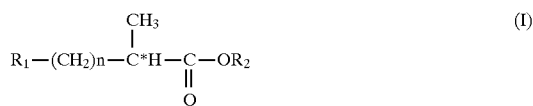

wherein $R_1$ is;

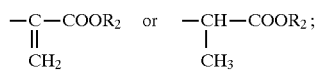

$R_2$ is a hydrogen atom or an alkyl group with 1–6 carbon atoms; n is an integer of 1 or 2; and * represents an asymmetric carbon atom.

2. The compound of claim 1, which is an optically active dicarboxylic acid derivative represented by the general formula (Ia):

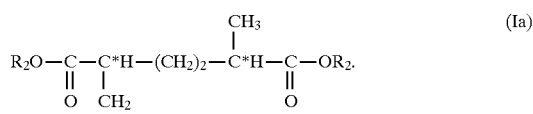

3. The compound of claim 1, which is an optically active, unsaturated dicarboxylic acid derivative represented by the general formula (Ib):

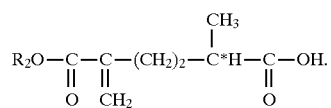

4. The compound of claim 1, which is an optically active, unsaturated dicarboxylic acid derivative represented by the general formula (Ic):

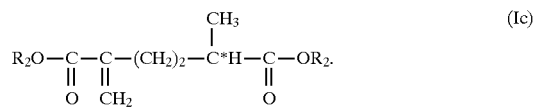

5. A method for producing an optically active α-substituted carboxylic acid derivative represented by the general formula (I') below and/or an antipode thereof:

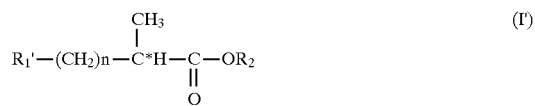

which method comprises allowing a culture, cells or a material obtained from cells of a microorganism selected from the group consisting of *Escherichia coli* MR-2103 (FERM BP-3835). *Pseudomonas putida* MR-2068 (FERM BP-3846) and a genetically engineered microorganism which has been transformed with a gene coding for an esterase that asymmetrically hydrolyzes ester bonds, which gene is obtained from *Escherichia coli* MR-2103 (FERM BP-3835) or *Pseudomonas putida* MR-2068 (FERM BP-3846), to act upon a racemic α-substituted carboxylic acid ester represented by the general formula (II):

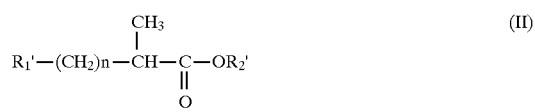

wherein $R_1'$ is a hydrogen atom, a hydroxyl group,

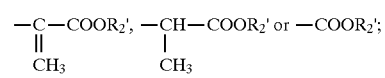

n is an integer of 1 to 4: $R_2'$ is an alkyl group with 1–6 carbon atoms; $R_2$ is a hydrogen atom or an alkyl group with 1–6 carbon atoms: and * represents an asymmetric carbon atom.

6. The method according to claim 5, wherein the racemic α-substituted carboxylic acid ester is a racemic, unsaturated dicarboxylic acid diester represented by the general formula (IIb):

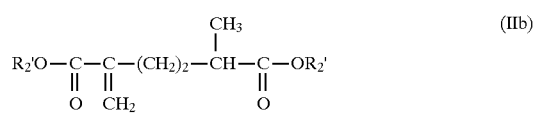

and the optically active α-substituted carboxylic acid derivative is an optically active, unsaturated dicarboxylic acid monoester represented by the general formula (Ib'):

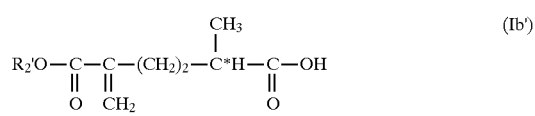

and the antipode is an antipodal ester represented by the general formula (Ic'):

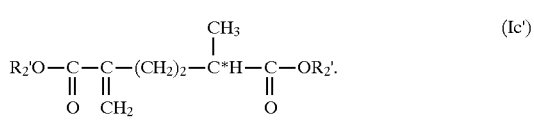

7. The method according to claim 5, wherein the racemic c-substituted carboxylic acid ester is a racemic α-methylalkanedicarboxylic acid diester represented by the general formula (IIe):

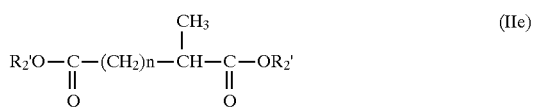

and the optically active α-substituted carboxylic acid derivative is an optically active α-methylalkanedicarboxylic acid-ω-monoester represented by the general formula (Ie'):

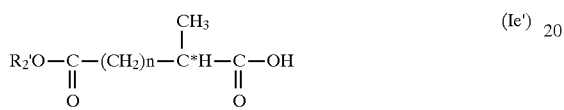

and the antipode is an antipodal diester represented by the general formula (Ie"):

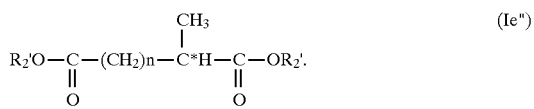

wherein for (IIe), (Ie') and (Ie") n is an integer of 1 or 2.

8. A method for producing an optically active β-hydroxycarboxylic acid and/or an antipodal ester thereof, which method comprises allowing a culture, cells or a material obtained from cells of a microorganism selected from the group consisting of *Escherichia coli* MR-2103 (FERM BP-3835), *Pseudomonas putida* MR-2068 (FERM BP-3846) and a genetically engineered microorganism which has been transformed with a gene coding for an esterase that asymmetrically hydrolyzes ester bonds, which gene is obtained from *Escherichia coli* MR-2103 (FERM BP-3835) or *Pseudomonas putida* MR-2068 (FERM BP-3846), to act upon a racemic β-hydroxycarboxylic acid ester to thereby obtain an optically active β-hydroxycarboxylic acid and/or an antipodal ester thereof.

9. A method for producing an optically active α-substituted carboxylic acid derivative represented by the general formula (Ia'):

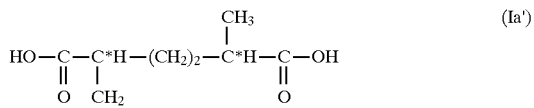

and/or an antipodal diester thereof represented by the general formula (Ia")

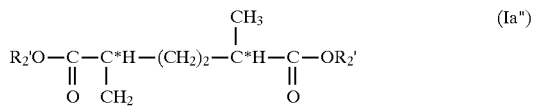

which method comprises allowing a culture, cells or a material obtained from cells of a microorganism selected from the group consisting of *Escherichia coli* MR-2103 (FERM BP-3835), *Pseudomonas putida* MR-2068 (FERM BP-3846) and a genetically engineered microorganism which has been transformed with a gene coding for an esterase that asymmetrically hydrolyzes ester bonds, which gene is obtained from *Escherichia coli* MR-2103 (FERM BP-3835) or *Pseudomonas putida* MR-2068 (FERM BP-3846), to act upon a racemic dicarboxylic acid ester represented by the general formula (IIa):

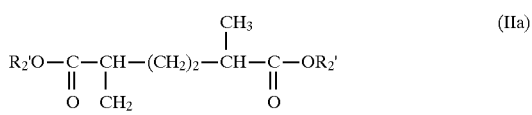

wherein $R_2'$ is an alkyl group with 1–6 carbon atoms and * represents an asymmetric carbon atom.

10. A method for producing an optically active α-methylalkanoic acid represented by the general formula (Id'):

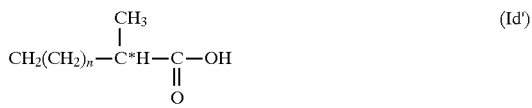

and/or an antipodal ester thereof represented by the general formula (Id")

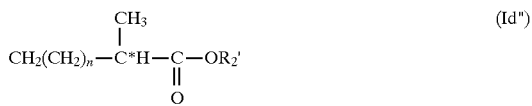

which method comprises allowing a culture, cells or a material obtained from cells of a microorganism selected from the group consisting of *Escherichia coli* MR-2103 (FERM BP-3835), *Pseudomonas putida* MR-2068 (FERM BP-3846) and a genetically engineered microorganism which has been transformed with a gene coding for an esterase that asymmetrically hydrolyzes ester bonds, which gene is obtained from *Escherichia coli* MR-2103 (FERM BP-3835) or *Pseudomonas putida* MR-2068 (FERM BP-3846), to act upon a racemic α-methylalkanoic acid ester represented by the general formula (IId):

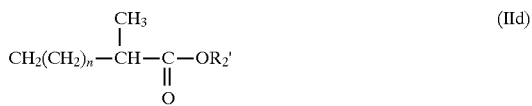

wherein $R_2'$ is an alkyl group with 1–6 carbon atoms, n is an integer of 1 to 3, and * represents an asymmetric carbon atom.

* * * * *